(12) United States Patent
Boulanger (10) Patent No.: US 12,318,547 B2
(45) Date of Patent: Jun. 3, 2025

(54) APPARATUS FOR SUPPLYING THERAPEUTIC GAS TO A PATIENT, WITH CONTROL OF THE PRESSURE AT THE MASK

(71) Applicant: L'Air Liquide, Société Anonyme pour l'Etude et l'Exploitation des Procédés Georges Claude, Paris (FR)

(72) Inventor: Thierry Boulanger, Philadelphia, PA (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 792 days.

(21) Appl. No.: 17/592,927

(22) Filed: Feb. 4, 2022

(65) Prior Publication Data
US 2022/0241545 A1  Aug. 4, 2022

(30) Foreign Application Priority Data
Feb. 4, 2021 (FR) ...................................... 2101085

(51) Int. Cl.
*A61M 16/20* (2006.01)
*A61M 16/00* (2006.01)
(Continued)

(52) U.S. Cl.
CPC ...... *A61M 16/203* (2014.02); *A61M 16/0003* (2014.02); *A61M 16/1005* (2014.02);
(Continued)

(58) Field of Classification Search
CPC ........... A61M 16/0057–0084; A61M 16/0078; A61M 16/0081; A61M 2205/15
See application file for complete search history.

(56) References Cited

U.S. PATENT DOCUMENTS

| 7,438,073 B2* | 10/2008 | Delache ............ A61M 16/0069 128/204.23 |
| 2006/0130835 A1* | 6/2006 | Truschel ............ A61M 16/204 128/204.23 |
| 2019/0336713 A1* | 11/2019 | Piracha ............... A61M 16/208 |

FOREIGN PATENT DOCUMENTS

| EP | 3 698 833 | 8/2020 |
| WO | WO 2011 089491 | 7/2011 |
| WO | WO 2017 006253 | 1/2017 |

OTHER PUBLICATIONS

Borrello, M. et al., A feedback control approach to the estimation of patent airway and leak flow for non-invasive, positive pressure ventilation (NPPV), 2016 American Control Conference (ACC), Jul. 6-8, 2016, Boston, MA, 3982-3987.
(Continued)

*Primary Examiner* — Kendra D Carter
*Assistant Examiner* — Mautin I Ashimiu
(74) *Attorney, Agent, or Firm* — Allen E. White (57) ABSTRACT

The invention relates to a gas delivery apparatus (1) having an internal gas passage (100), a deformable reservoir (27), a valve device (22), and a control unit (50) with microprocessor (51) controlling the valve device (22) in order to set or adjust the flow rate of gas passing through said valve device (22). A flow rate determination device (60) makes it possible to perform measurements of pressure or flow rate in the internal gas passage (100) and to transmit these measurements to the control unit (50). A pressure sensor (55) performs gas pressure measurements ($P_{55}$) on the therapeutic gas feeding the deformable reservoir (27) and supplies them to the control unit (50). A breathing mask (10) is in fluidic communication with the internal gas passage (100) in order to be fed with therapeutic gas coming from the deformable reservoir (27).

15 Claims, 3 Drawing Sheets

(51) Int. Cl.
*A61M 16/06* (2006.01)
*A61M 16/10* (2006.01)
*A61M 16/12* (2006.01)

(52) U.S. Cl.
CPC ........ *A61M 16/105* (2013.01); *A61M 16/109* (2014.02); *A61M 16/12* (2013.01); *A61M 16/208* (2013.01); *A61M 2016/0027* (2013.01); *A61M 2016/0033* (2013.01); *A61M 2202/02* (2013.01); *A61M 2202/0283* (2013.01)

(56) References Cited

OTHER PUBLICATIONS

French Search Report for corresponding FR 2101085, Oct. 18, 2021.

* cited by examiner

APPARATUS FOR SUPPLYING THERAPEUTIC GAS TO A PATIENT, WITH CONTROL OF THE PRESSURE AT THE MASK

CROSS REFERENCE TO RELATED APPLICATIONS

This application claims the benefit of priority under 35 U.S.C. § 119 (a) and (b) to French Patent Application No. 2101085, filed Feb. 4, 2021, the entire contents of which are incorporated herein by reference.

BACKGROUND

The invention relates to a gas delivery apparatus for supplying a therapeutic gas (i.e. pure gas or a gas mixture) to a conscious patient in different care locations, in particular in hospital, including for inhalations over a long period of time, for example several hours, while minimizing gas losses.

Certain therapies require that therapeutic gas made up of a mixture of several gaseous constituents be administered to conscious patients. It is thus known to use an equimolar mixture (50%/50%) of nitrous oxide ($N_2O$) and oxygen ($O_2$) in order to reduce anxiety, produce a sedative effect and/or alleviate acute pain. Likewise, it has been proposed to use a mixture of argon and oxygen (60 vol % Ar/40 vol % $O_2$), inhaled before and during, or even after, a mechanical thrombectomy procedure, in order to treat cerebrovascular accidents (CVA).

Although the administration of the gas by inhalation is generally short, that is to say typically less than 30 minutes, longer inhalation, of the order of 1 hour or more, is sometimes necessary.

Generally, the therapeutic gas (i.e. one or more constituents) is inhaled via a breathing mask, typically a face mask, i.e. a naso-buccal mask, by a conscious patient, either continuously or intermittently, that is to say periodically.

The intermittent, that is to say non-continuous, delivery of gas is often preferred. To this end, devices called "demand valves" are conventionally used.

However, a demand valve also has its drawbacks. Thus, a demand valve requires a relatively significant minimum negative pressure in order to open and supply the flow rate of gas to the patient and, once open, a considerable inspiratory effort by the patient is needed in order to inhale the gas the patient needs. This drawback may be made worse when tubes measuring several metres have to be used, since these will generate an additional resistance to inhalation, which is damaging in the case of weak patients. Moreover, the negative pressure generated at the mask often entrains ambient air (i.e. lack of leaktightness) which dilutes the therapeutic gas and has a negative impact on the efficacy of the therapeutic gas administered to the patient.

For these reasons, demand valves are contra-indicated for certain patients, in particular weak individuals (e.g. infants, the elderly, etc.), and also for treatment of certain pathologies, in particular those affecting these types of patient, for example cardiovascular accidents, which are suffered for the most part by the elderly.

EP-A-3698833 proposes a device for automatic delivery of therapeutic gas to a patient, comprising a gas passage with a valve device for controlling the flow rate of gas feeding a deformable reservoir, a control unit with microprocessor for controlling the valve device in order to set or adjust the flow rate of gas, flow rate determination means for transmitting measurements to the control unit, a differential pressure sensor for performing gas flow rate measurements downstream of the deformable reservoir and for supplying them to the control unit, and a breathing mask fed with therapeutic gas coming from the deformable reservoir. This device is able to facilitate breathing in weak patients, especially those with COPD. Although the device, which functions similarly to a demand valve, is able to facilitate the respiratory work of the patient, it is not able to limit the dilution of the therapeutic gas in the event of a loss of leaktightness at the mask, because the tubes of several metres situated between the device and the patient generate a resistance to the flow of the gas and thus produce a negative pressure in the mask.

Furthermore, M. Borello et al., "A feedback control approach to the estimation of the patient airway and leak flow for non-invasive positive pressure ventilation (NPPV), Jul. 6-8, 2016, American Control Conference (ACC)" and WO-A-2017/006253 propose an algorithm permitting estimation of the respiratory flows and leaks in the case of non-invasive ventilation performed on patients in critical care. The algorithm is based on simple feedback control, measurements of proximal pressure, the inlet flow of the medical ventilator supplying the assistance gas, and a non-linear model of the connecting circuit. The teaching of these documents concerns a proximal pressure measurement and a restoration of the flow rate at the mask via this measurement of this pressure, a flow rate measurement in the ventilator, and a circuit model.

Finally, WO-A-2011/089491 teaches a system for controlling and regulating a flow of gas supplied to a patient from a pressure generator that feeds a patient circuit connected to the patient. A flow rate sensor measures the flow rate and a controller determines one or more parameters of the respiratory flow and uses these parameters to calculate a breath-amplitude-based target parameter and a time-based parameter of each respiratory cycle of the patient. This system is aimed at a target volume, taking account of the intentional leak of the mask in order to seek to compensate for the volume of gas that escapes from it.

These solutions are reserved to a particular type of gas administration device, since the restoration of a signal useful for their functioning is based on a proximal pressure measurement issuing from a pressure sensor situated at the patient's mask. Such a sensor makes the mask heavy, which can cause sudden leaks. Since they operate in positive pressure and thus prevent any introduction of gas into the patient's mask, a proximal pressure measurement makes it possible to ensure good ventilation of the patient, but by causing discomfort to the patient. This is not applicable, however, in the context of a system operating in the manner of a demand valve, that is to say functioning in "negative" pressure.

In this context, a problem lies in making available an apparatus for delivering therapeutic gas, i.e. pure gas or a gas mixture, to a patient, making it possible to limit the consumption of gas, that is to say functioning in a similar way to a demand valve (with "negative" pressure), while ensuring minimal inspiratory effort on the part of the patient in order to ensure their respiratory comfort, including during long procedures (e.g. one to two hours or more), and limiting as far as possible the dilution of the therapeutic gas in the event of leaks at the mask and undesirable ingress of ambient air due to defective sealing, that is to say an apparatus which avoids all or some of the problems encountered with demand valves during intermittent, that is to say non-continuous, gas delivery to a patient who needs to inhale a therapeutic gas in the context of medical treatment.

SUMMARY

A solution according to the invention relates to an apparatus for delivering therapeutic gas to a patient, comprising:
- an internal gas passage in fluidic communication with a deformable reservoir in order to feed the deformable reservoir with therapeutic gas and to recover therapeutic gas coming from said deformable reservoir,
- a valve device arranged on the internal gas passage, upstream of the deformable reservoir, in order to control the flow rate of therapeutic gas feeding the deformable reservoir,
- a control unit with microprocessor controlling the valve device in order to set or adjust the flow rate of gas passing through said valve device,
- flow rate determination means designed to perform one or more measurements of pressure or flow rate in the internal gas passage and to transmit said measurement(s) to the control unit,
- a pressure sensor configured to perform one or more gas pressure measurements ($P_{55}$) on the therapeutic gas feeding the deformable reservoir and to supply said gas pressure measurement(s) ($P_{55}$) to the control unit, and
- a breathing mask in fluidic communication with the internal gas passage and fed with therapeutic gas coming from the deformable reservoir, and wherein:
- the pressure sensor is arranged on the internal gas passage upstream of the deformable reservoir and
- the control unit is configured to:
  - i) determine the flow rate of gas ($Q_{60}$) circulating in the internal gas passage on the basis of the one or more pressure or flow rate measurements supplied by the flow rate determination means,
  - ii) determine the gas pressure on the basis of the one or more gas pressure measurements ($P_{55}$) coming from the pressure sensor,
  - iii) determine the losses of head ($\Delta P$) downstream of the pressure sensor on the basis of the gas flow rate ($Q_{60}$),
  - iv) determine the pressure ($P_M$) at the breathing mask on the basis of the gas pressure ($P_{55}$) and of the losses of head ($\Delta P$),
  - v) and control the valve device to adjust the gas flow rate according to said pressure ($P_M$) determined at the breathing mask, in such a way as to adjust the pressure at the breathing mask to a value equal to atmospheric pressure.

In the context of the invention:
- the term "pressure" is used to generally denote a positive pressure (>0 bar), zero pressure (=0 bar) or negative pressure (<0 bar).
- the pressures are expressed in bar or mbar relative.
- the "−" sign before a pressure value denotes that the pressure is negative (i.e. below atmospheric pressure).
- the "+" sign before a pressure value denotes that the pressure is positive (i.e. above atmospheric pressure).
- the term "therapeutic gas" denotes a gas with one or more gaseous constituents or compounds, that is to say a "pure" gas or a gas mixture.
- in "control unit", the term "unit" is equivalent to the terms "devices", "apparatus", "means", "system" or similar, and the term "control" is equivalent to the terms "command", "guidance", "processing" or similar.

Depending on the embodiment considered, the apparatus according to the invention for delivering therapeutic gas can comprise one or more of the following features:
- the control unit (50) is configured to determine the losses of head ($\Delta P$) using a stored calculation formula, namely: $\Delta P = R \ast Q_{60}^2$ where:
  - R is a constant.
  - $Q_{60}$ is the flow rate of gas ($Q_{60}$) circulating in the internal gas passage.
- the flow rate determination means are designed to perform one or more measurements of pressure or flow rate in the internal gas passage, downstream of the deformable reservoir.
- the flow rate determination means comprise a pressure sensor or a flow rate sensor, in particular a differential pressure sensor or a mass-flow sensor.
- it comprises storage means for storing the formula for calculating the losses of head ($\Delta P$).
- the valve device comprises a proportional valve.
- the pressure sensor is arranged on the internal gas passage between the valve device and the deformable reservoir.
- it further comprises at least one non-return device arranged in the internal gas passage, downstream of the deformable reservoir.
- at least one non-return device comprises a non-return valve.
- the breathing mask is in fluidic communication with the internal gas passage via a flexible gas conduit, i.e. a flexible tube or the like.
- the control unit comprises at least one electronic board carrying at least one microprocessor.
- the gas conduit comprises a filtration means, in particular a heat and humidity exchange filter.
- the internal gas passage comprises one or more conduits, tubes or similar.
- the flow rate determination means are electrically connected to the control unit.
- the pressure sensor is configured to supply the control unit with one or more pressure measurements, preferably several successive pressure measurements, in the form of numerical values or signals representing such numerical values (for example voltage signals), which values or signals can be processed as they are or can be converted into numerical values by the control unit.
- the pressure sensor is configured or controlled in order to perform pressure measurement at given time intervals, preferably every 20 msec or less, preferably every 10 msec or less, or even every 5 msec or less.
- the pressure sensor is a relative pressure sensor comprising a detection orifice arranged in the internal gas passage, and moreover referenced to atmospheric pressure (i.e. 0 mbar=1 atm).
- the pressure sensor is a relative pressure sensor configured to supply one or more gas pressure measurements ($P_{55}$), each corresponding to a difference between the absolute pressure determined at the detection orifice (55*a*) and the atmospheric pressure.
- it comprises an electrical power source of the cord and mains plug type (e.g. 110/220 V) and/or an internal battery, preferably rechargeable.
- the electrical power source supplies electrical current to the control unit and all of the other components of the apparatus present (depending on the chosen embodiment) that require electrical power to operate, for example one or more components such as a display screen, LED, acoustic and/or visual alarm device, etc.
- it comprises a rigid outer casing, for example made of polymer or other material.

the control unit, at least part of the internal gas passage, the deformable reservoir, the flow rate determination means and/or the valve device are arranged in the casing.

the deformable reservoir comprises a flexible balloon or similar.

the deformable reservoir deforms depending on the quantity and/or the pressure of therapeutic gas that it contains. It can therefore adopt different states, stages or levels of filling, in particular a "full" stage, an "empty" stage (i.e. minimal residual quantity of gas) and intermediate stages corresponding to partial filling of the reservoir (i.e. between the "full" and "empty" stages).

the deformable reservoir is made from flexible material of the rubber or silicone type or similar, for example a NuSil LSR silicone rubber.

the control unit with microprocessor comprises one or more microprocessors, preferably one or more microcontrollers.

the one or more microprocessors use one or more algorithms.

the control unit comprises one or more data storage memories or similar, for example one or more calculation formulas, reference tables, etc.

the control unit with microprocessor comprises an electronic board holding the one or more microprocessors, preferably one or more microcontrollers.

the deformable reservoir has a volume of between about 0.1 and 3 L, measured at rest (i.e. internal pressure equal to atmospheric pressure).

the deformable reservoir has a wall with a thickness of between 0.10 and 0.90 mm, typically between 0.25 and 0.75 mm.

the apparatus further comprises one or more one-way valves arranged in the internal gas passage, in particular downstream of the deformable reservoir.

the apparatus further comprises a human-machine interface (HMI) comprising an information display screen, preferably a touch screen, and/or one or more selection keys or buttons, in particular virtual keys that are displayed on the touch screen, and/or a starting device, such as an on/off button, and/or other elements.

the apparatus further comprises an alarm system for alerting the user in the event of a problem affecting the apparatus or the gas, for example a valve or sensor fault, an incorrect gas composition (e.g. hypoxic mixture) or other problems. The alarm system can comprise means or a device for emitting audible and/or visible signals.

the breathing mask is a face mask covering the patient's nose and mouth in use, that is to say when it is worn by said patient.

it further comprises a therapeutic gas source fluidically connected to the internal gas passage in order to feed said gas passage with therapeutic gas.

the source of therapeutic gas comprises one or more gas containers, in particularly cylinders.

the source of therapeutic gas comprises a gas container containing an $O_2/N_2O$ gas mixture, preferably an equimolar $O_2/N_2O$ mixture (i.e. 50 mol %/50 mol %).

alternatively, the source of therapeutic gas comprises a gas container containing an $O_2$/argon gas mixture, preferably containing 35 to 45 vol % $O_2$ and 55 to 65 vol % Ar, for example a mixture containing 38 to 43 vol % $O_2$ and 57 to 62 vol % Ar, particularly a binary mixture made up of 40 vol % $O_2$ and 60 vol % Ar.

alternatively, the source of therapeutic gas comprises a first gas container containing argon or $N_2O$, a second gas container containing oxygen ($O_2$), and a gas mixer fed with gas by said first and second gas containers, said mixer performing mixing of the gases coming from the first and second gas containers, in order to obtain an $O_2/N_2O$ or $O_2$/argon gas mixture.

it comprises a pressure supply conduit, i.e. a pneumatic connection, arranged between the breathing mask and the pressure sensor of the gas delivery apparatus.

The invention further relates to a method for treating a patient by administering a therapeutic gas to the patient's airways using a gas delivery apparatus for supplying the therapeutic gas, i.e. pure gas or a gas mixture, to the conscious patient, in particular in hospital, in particular in the context of inhalation for a long period of time, for example several hours, while minimizing gas losses.

For example, the treatment method can comprise the administration to the patient, by inhalation, of a mixture of nitrous oxide ($N_2O$) and oxygen ($O_2$), as equimolar $N_2O/O_2$ (i.e. 50%/50%), intended to treat a state of anxiety, produce a sedative effect or alleviate acute pain, or a mixture of argon and oxygen (e.g. 60 vol. % Ar/40 vol. % $O_2$), inhaled for example before and during, or even after, a mechanical thrombectomy procedure, in order to treat cerebrovascular accidents (CVA) or the like.

BRIEF DESCRIPTION OF THE DRAWINGS

The invention will now be better understood from the following detailed description given as a non-limiting example and with reference to the appended figures, in which.

DETAILED DESCRIPTION OF PREFERRED EMBODIMENTS

Figure 1:
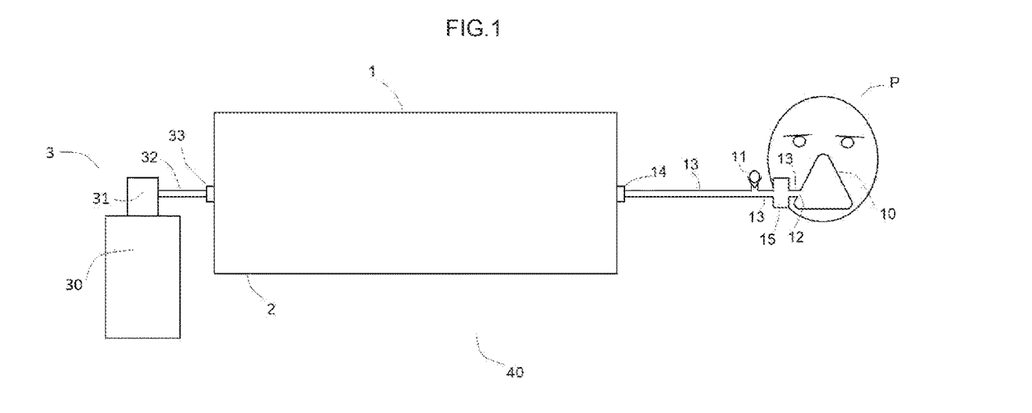
FIG. 1 shows schematically the supply of therapeutic gas to a patient with the aid of a gas supply apparatus according to the invention.
Figure 2:
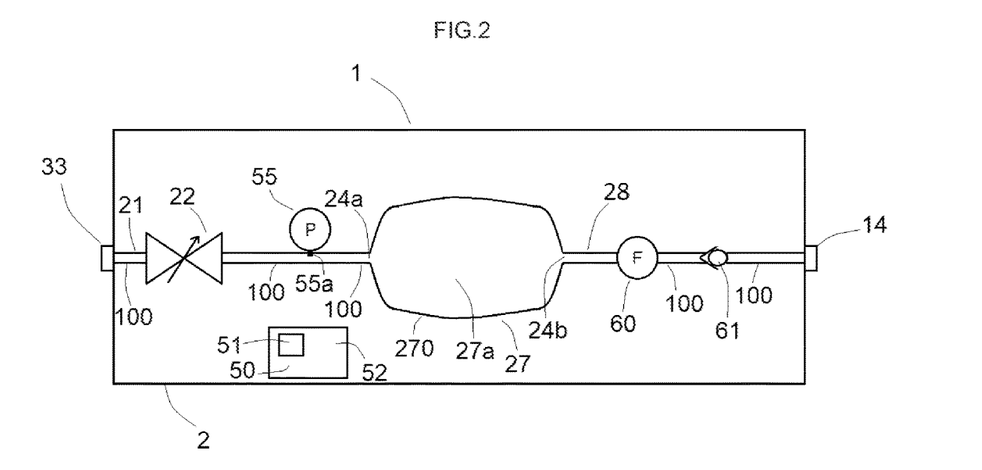
FIG. 2 shows schematically an embodiment of the internal architecture of a gas supply apparatus according to the invention, FIG. 3 details the elements arranged downstream of the pressure sensor of the gas delivery apparatus of FIG. 2.

FIG. 1 is a schematic representation of the supply of therapeutic gas to a patient using a gas supply apparatus 1 according to the present invention, in particular the one shown schematically in FIG. 2.

This apparatus 1 comprises an outer casing 2 forming a rigid shell, for example made from polymer, comprising the internal components, in particular an internal gas passage, a deformable reservoir, a valve device, and a control unit with microprocessor as explained below.

A source 3 of therapeutic gas, such as a gas cylinder 30 provided with a distributor valve 31, supplies a therapeutic gas, that is to say a gas or a gas mixture, to the gas delivery apparatus 1 via a connecting hose 32, which is connected to an inlet port 33 of the apparatus 1.

The therapeutic gas passes through the gas delivery apparatus 1, as is explained below, in order then to be delivered to a patient P by way of a flexible gas conduit 13, such as a flexible tube made of polymer, which is fluidically connected to an outlet port 14 of the apparatus 1. The gas is supplied to the patient P via a respiratory interface or breathing mask 10 supplied via the flexible gas conduit 13.

Preferably, the respiratory interface or breathing mask 10 is a face mask, i.e. a naso-buccal mask, covering the patient's mouth and nose. Other respiratory interfaces may of course be suitable and are chosen depending on the treatment that is to be administered to the patient.

The face mask 10 here has an inhalation port 12 fluidically connected to the gas conduit 13 that conveys the gas. A filter 15 is arranged in the gas conduit 13.

An exhalation port 11 is arranged in said gas conduit 13, upstream of the filter 15. The exhalation port 11 is closed by a non-return valve 11a which controls the emerging flow of gas by permitting the discharge of the exhaled gases to the atmosphere, during the exhalation phases of the patient P, i.e. the exhaled gases rich in $CO_2$, and also by preventing ambient air from entering the gas conduit 13 when the patient inhales the therapeutic gas, that is to say during their inhalation phases. The non-return valve 11a comprises a one-way valve, such as a silicone disc resting on a perforated surface, which only allows the gas to pass through in one direction, for example the one-way valve with part reference 97351 sold by Qosina.

The filter 15, making it possible to limit the exposure of the patient to fine particles or to potential bacteria or other microorganisms, is preferably a heat and humidity exchange filter. The gas mixture contained in the gas cylinder 30 is in fact a dry gas, that is to say deprived of water vapour. If there is no humidifying of the inhaled gases over a period of several hours, the respiratory system of the patient P may become dry, which causes discomfort or even lesions. A heat and humidity exchange filter 15 captures the humidity present in the gases exhaled by the patient and in so doing heats up (on account of the exhaled gases being at body temperature, i.e. approximately 32° C.) when they pass through the filter 15, to be evacuated to the ambient atmosphere via the exhalation port 11. This same filter heats and then releases this humidity into the therapeutic gas, during the subsequent inhalation. Such filters are well known, and it is possible, for example, to use a Hydro-Therm® filter sold by Intersurgical.

The gas source 3 contains a pressurized therapeutic gas, for example an argon/oxygen mixture, for example comprising 60 vol % argon and 40 vol % oxygen, at a maximum pressure of the order of 250 bar. The distributor valve 31 is preferably an integrated pressure regulator valve delivering the gas to the connecting hose 32 at a reduced pressure, for example of the order of 5 bar. The integrated pressure regulator 31 is preferably protected by a rigid cap (not shown).

Alternatively, the gas source 3 can comprise several gas containers 30, for example a first container containing argon, a second container containing oxygen ($O_2$), and a gas mixer fed with gas by said first and second containers in order to produce the desired $O_2$/argon gas mixture, which is then supplied to the gas delivery apparatus 1 according to the present invention.

Of course, the gas delivery apparatus 1 according to the present invention can also be used to supply other therapeutic gases such $O_2/N_2O$ or the like.

FIG. 2 shows schematically an embodiment of the internal architecture of the gas delivery apparatus 1 according to the present invention, which forms part of the gas supply installation 40 according to the present invention, which is shown schematically in FIG. 1.

The gas delivery apparatus 1 comprises a control unit 50 comprising one or more microprocessors 51 carried by an electronic board 52 used to control a valve device 22, preferably a proportional valve, in order to set or adjust the gas flow rate passing through said valve device 22, as is explained below.

The control unit 50 comprises one or more microprocessors 51, typically one or more microcontrollers, executing one or more algorithms, which receive and analyse the measurements supplied by various sensors, in particular by a pressure sensor 55 and flow rate determination means 60 arranged in the casing 2.

An internal gas passage 100, for example a conduit or similar, is arranged in the casing 2 and extends between an inlet port or orifice 33 and an outlet port or orifice 14, so as to convey the therapeutic gas from the inlet port 33 to the outlet port 14 and then allow it to be conveyed to the mask 10, via the flexible conduit 13.

The valve device 22, namely a proportional valve here, is arranged in the internal gas passage 100, preferably in the upstream section 21 of said internal gas passage 100. It is controlled by the microcontroller 51 of the control unit 50 in order to modify the flow rate of therapeutic gas passing through said valve device 22 and circulating in the lumen of the internal gas passage 100 towards the outlet port or orifice 14.

Various types of proportional valves can be used as valve device 22; preferably, a proportional valve is chosen that operates over a wide range of flow rates, for example the valve designated as IMI FAS FLATPROP.

A pressure sensor 55 is arranged in the internal gas passage 100, at the outlet of the valve device 22. More precisely, the pressure sensor 55 is arranged between the valve device 22 and the deformable reservoir 27, so as to perform pressure measurements in the internal gas passage 100 and upstream of the deformable reservoir 27, as is explained below.

The pressure sensor 55 is configured to measure negative pressures (that is to say pressures below atmospheric pressure) and positive pressures (that is to say pressures above atmospheric pressure, or overpressures), for example in the range from −10 mbar to +10 mbar.

The pressure sensor 55 here is a relative pressure sensor which comprises a detection orifice 55a arranged in the internal gas passage 100, and which is moreover referenced to atmospheric conditions, i.e. to atmospheric pressure (i.e. 0 mbar=1 atm). In other words, the pressure returned by the pressure sensor 55 is the difference between the absolute pressure prevailing at its detection orifice 55a, which reflects the pressure in the internal gas passage 100, and atmospheric pressure. For example, it is possible to use a relative pressure sensor such as the True Stability® sensor available from Honeywell.

The internal gas passage 100 then conveys the gas to a deformable reservoir 27, in particular a flexible reservoir, positioned downstream of the pressure sensor 55 and fluidically connected to the gas passage 100. The deformable reservoir 27 comprises a flexible peripheral wall 270 defining an internal volume 27a for the gas, forming a deformable pouch for the therapeutic gas. At rest, the internal volume 27a is, for example, between approximately 0.1 and 1 L.

The gas flow enters the internal volume 27a of the deformable reservoir 27 through a reservoir inlet orifice 24a, in fluidic communication with the internal gas passage 100.

Preferably, the properties of the deformable reservoir 27 are such that it is highly deformable. For example, its peripheral wall 270 has a thickness of between approximately 0.25 and 0.75 mm and is made from a biocompatible flexible silicone, for example a silicone material from the LSR range sold by NuSil.

The gas leaves the reservoir 27 through a reservoir outlet orifice 24b that is fluidically connected to a downstream section 28 of the internal gas passage 100, extending as far as the outlet port 14.

Flow rate determination means 60, namely a flow rate sensor or a pressure sensor, are arranged in the downstream section 28 of the internal gas passage 100, in order to measure the flow rate or the pressure of therapeutic gas circulating in said downstream section 28. The flow rate determination means 60 can be a mass-flow sensor or a differential pressure sensor.

The flow rate determination means 60 are electrically connected to the control unit 50 and deliver one or more flow rate or pressure signals that are processed by the control unit 50, typically by the microprocessor 51, preferably a microcontroller.

Preferably, a volumetric flow rate is obtained after conversion of the signal supplied by the flow rate determination means 60 using a specific look-up table stored in a memory interacting with the control unit 50.

Finally, one or more non-return devices 61, such as a non-return valve, are arranged in the internal gas passage 100, namely downstream of the flow rate determination means 60 and upstream of the outlet port 14 of the casing 2, in order to prevent any backflow of gas. Thus, the gases exhaled by the patient P are discharged solely through the exhalation port 11 of the mask 10 and cannot return to the reservoir 27.

Moreover, an electrical power source (not shown) supplies electrical current to all of the components that operate using electrical energy, such as sensors, control unit, controlled valves, human-machine interface (HMI), digital display screen, etc. It can be positioned in the casing 2, for example a rechargeable battery, or comprises a cord and a mains plug (110/220 V), and optionally a current converter.

At successive time intervals, for example every 5 msec, the pressure sensor 55 sends a pressure measurement signal ($P_{55}$) to the control unit 50. This signal $P_{55}$ reflects the pressure prevailing, at the time in question, at the detection orifice 55a of the pressure sensor 55, which is arranged in the internal gas passage 100.

Similarly, the flow rate determination means 60 send, for example every 5 msec, a flow rate measurement signal Q (or differential pressure signal permitting calculation of the flow rate Q) to the control unit 50. The signal Q reflects the flow rate of gas circulating in the internal gas passage 100 and, by extension, in the gas conduit 13.

The control unit 50 then processes these pressure and flow rate signals in order to control the proportional valve 22 as set out in detail below, in order to adjust the flow rate of gas sent to the flexible reservoir 27.

The flexible reservoir 27 has various inflation/deflation states depending on the gas pressure prevailing there, and therefore depending on the quantity of gas that is introduced into it or withdrawn from it, comprising at least:
- a "rest" state, in which the internal volume 27a, filled with gas, is at atmospheric pressure (i.e. 1 atm).
- an "inflated" state, in which the internal volume 27a, filled with gas, is at a pressure higher than ambient pressure (i.e. >1 atm).
- "partially deflated" states, in which some of the gas contained in the reservoir has left it.

Figure 3:
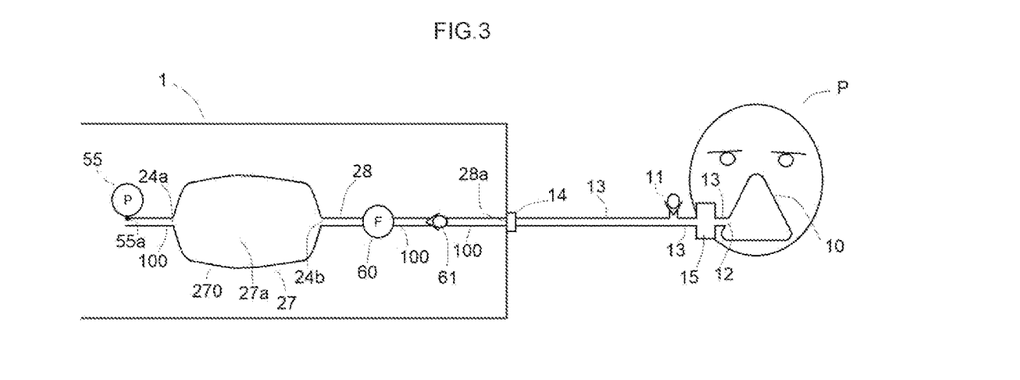
Figure 4:
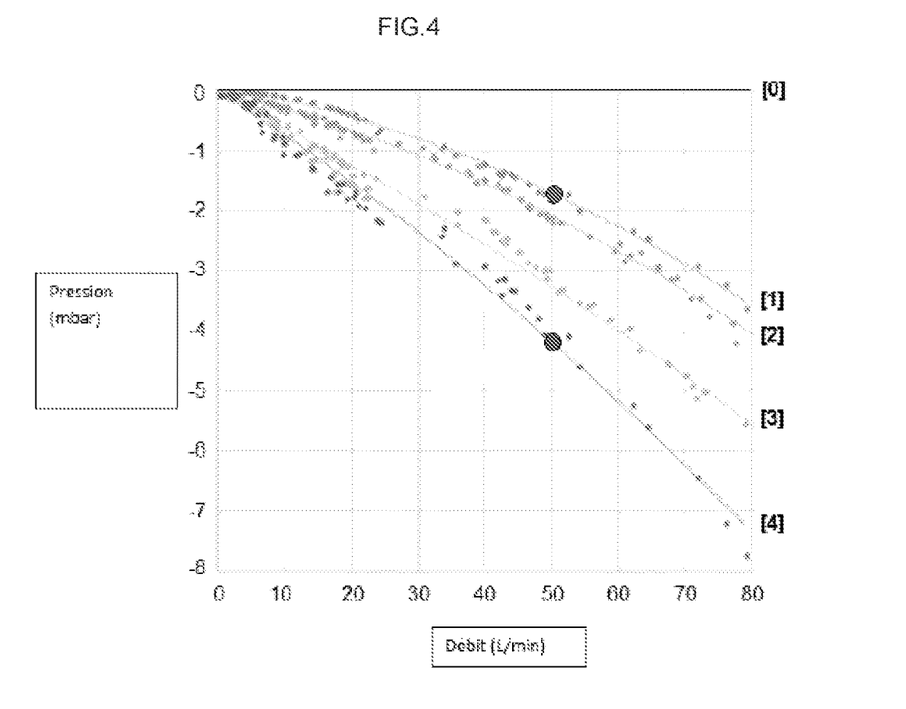
FIG. 4 shows schematically the pressure/flow rate relationship of the elements from FIG. 3.

FIG. 3 shows in detail the elements arranged downstream of the pressure sensor 55 of the gas delivery apparatus 1, as far as the patient P, and FIG. 4 shows schematically the pressure/flow rate relationship of these different elements, that is to say the resistance (i.e. a pressure) to the flow of a gas (i.e. a flow rate) passing through them.

A patient P is first of all fluidically connected to the elements situated downstream of the pressure sensor 55. The detection orifice 55a of the pressure sensor 55 is then at atmospheric pressure, that is to say the relative pressure measured is equal to 0 mbar.

In response to an inhalation by the patient P generating a given flow rate Q, this gas flow rate Q will circulate in the internal gas passage 100, especially at the detection orifice 55a of the pressure sensor 55. The gas pressure existing in the breathing mask 10 is then the resultant of the losses of head ($\Delta P$) of the different elements situated downstream of the pressure sensor 55.

The pressure/flow rate relationship is illustrated in FIG. 4, in which:
- The curve [0], which is equal to 0 mbar relative, that is to say to the ambient pressure, represents the pressure measured by the pressure sensor 55.
- The curve [1] represents the losses of head $\Delta P$ introduced between the pressure sensor 55 and the downstream termination 28a of the downstream section 28 of the internal gas passage 100. For example, for a flow rate Q of 50 L/min circulating in this portion, a negative pressure of −1.5 mb relative is necessary at the termination 28a.
- The curve [2] represents the additional losses of head generated by the outlet port 14 of the apparatus 1.
- The curve [3] represents the additional losses of head generated by the portion of the gas conduit 13 situated downstream of the filter 15.
- The curve [4] represents the additional losses of head generated by the filter 15, including the downstream portion of the gas conduit 13, as far as the inhalation port 12 of the breathing mask 10.

All of these additional losses of head add up, and, for a flow rate of 50 L/min, this leads to a negative pressure of the order of −4 mbar in the breathing mask 10. In other words, the patient P will have to make a considerable inspiratory effort to generate such a negative pressure.

It appears moreover that the pressure/flow rate relationship between the pressure sensor 55 and the pressure in the breathing mask, also called $P_{Mask}$ or $P_M$, increases when the flow rate increases. It follows a polynomial function of the following type:

$$P_M = -R*Q^2 \text{ where:}$$

R is a constant taking account of the "equivalent resistance" of the elements situated between the pressure sensor 55 and the breathing mask 10, and Q is the flow rate passing through said elements.

This polynomial function is also represented in FIG. 4 in the form of solid curves.

It will be appreciated that such a level of effort to be made by the patient is unacceptable and that, in the context of the invention, this pressure must necessarily be reduced to approximately 0 mbar relative, that is to say approximately the atmospheric pressure.

To do this, according to the invention, in knowledge of the losses of head ($\Delta P$) generated by the different elements downstream of the pressure sensor 55, it is possible to restore the pressure $P_M$ prevailing in the breathing mask 10.

In particular, considering that the pressure/flow rate relationship "$-R*Q^2$" is registered in the control unit 50 with microcontroller 51 in the form of one or more polynomial functions or an interpolation table, the restoration of the pressure at the mask $P_M$ can be effected by the control unit 50.

To this end, the control unit 50 performs the following calculation:

$$P_M = P_{55} - R*Q_{60}^2 \text{ where:}$$

$P_{55}$ is the pressure measured by the pressure sensor 55, and $Q_{60}$ is the flow rate circulating in the downstream section 28 of the internal gas passage 100, measured by the flow rate sensor 60.

Returning to the example of curve [4] (i.e. the pressure in the mask) and a flow rate $Q_{60}$ of 50 L/min, this gives: $P_M = P_{55} - 4$ (mbar)

In other words, for a relative pressure $P_{55}$ of zero, as is illustrated in FIG. 3, the resulting pressure in the mask is approximately −4 mbar.

In response to a flow rate measurement of 50 L/min by the flow rate determination means 60, the control unit 50 can control the proportional valve 22 to minimize the pressure $P_M$, that is to say to pressurize the internal gas passage 100 in such a way that, at the detection orifice 55a of the pressure sensor 55, the pressure is positive and, in this precise case, equal to approximately 4 mbar.

In other words, the control unit 50 controls the solenoid valve 22 in such a way that, in response to a flow rate demand of the patient P, the losses of head of the elements situated downstream of the pressure sensor 55 are compensated.

According to the invention, the control unit 50 can, at a time t, determine the pressure $P_M$ in the mask by proceeding as follows:

Determining the flow rate $Q_{60}$ circulating in the downstream section 28 of the internal gas passage 100, by way of the flow rate determination means 60.

Deducing therefrom the losses of head ($\Delta P$) induced by the elements situated downstream of the pressure sensor 55 via the registered function: $R*Q_{60}^2$.

Determining the pressure $P_{55}$ by means of the pressure sensor 55.

Deducing therefrom the pressure $P_M$ at the mask.

The pressure $P_M$ prevailing in the breathing mask 10, and determined in this way, is therefore a "restored pressure".

In the context of the invention, it is sought to minimize this "restored" pressure $P_M$ in the mask in order to lessen the inspiratory effort by the patient.

As is illustrated in FIG. 2, during therapy with administration of therapeutic gas, the patient P performs a succession of inhalations and exhalations in order to inhale the therapeutic gas, for example an $O_2$/argon or $N_2O/O_2$ mixture, and exhale the $CO_2$-rich gases resulting from the pulmonary exchanges.

In order to facilitate understanding of how the apparatus 1 works, it is considered that:
the pressure in the internal volume 27a of the reservoir 27 is equal to atmospheric pressure, that is to say the reservoir 27 is in the rest position.
the reservoir 27 is filled with the therapeutic gas coming from the gas source 3.
the patient is initiating an inhalation.

When the patient starts to inhale, a slight negative pressure occurs at the inhalation port 12 of the mask 10. This negative pressure spreads through the conduit 13, the outlet port 14 and the downstream section 28 of the internal gas passage 100.

While the gas pressure in the internal volume 27a of the reservoir 27 is equal to atmospheric pressure (i.e. 1 atm), a positive differential pressure then appears and a gas flow rate, measured by the flow rate determination means 60, can be established from the reservoir 27 in the direction of the mask 10. As a result, the internal volume 27a of the reservoir 27 then empties and the reservoir 27 deflates, in turn creating a slight negative pressure in the internal volume 27a.

The control unit 50 is configured to ensure that at any time the pressure prevailing in the mask 10 is as close as possible to atmospheric pressure (i.e. 1 atm), i.e. 0 mbar relative.

To do this, the control unit 50 controls the proportional valve 22 such that the flow rate supplied by said proportional valve 22 is proportional to the restored pressure $P_M$ in the mask 10.

To this end, the microprocessor 51 can for example implement an algorithm of the following type:
If "Mask pressure" is negative: Flow rate (L/min)=$\alpha*|P|$
If "Mask pressure" is positive: Flow rate (L/min)=0
where: $\alpha$ is a positive constant and $|P|$ is the absolute value of the restored pressure $P_M$ in the mask.

The control unit 50 therefore only acts on the proportional valve 22 if the restored pressure $P_M$ in the mask 10 is negative, that is to say the proportional valve 22 is controlled to or stays in the closed position as soon as the restored pressure in the mask 10 becomes positive.

In the case of a negative restored pressure in the mask 10, reflecting an inhalation by the patient P, the proportional valve 22 is controlled by the control unit 50 such that: Flow rate (L/min)=$\alpha*|P|$.

A proportionality then occurs between the flow rate delivered by the proportional valve 22 and the negative pressure restored in the mask 10. The further away the pressure value moves from 0 mb, the higher the flow rate. Conversely, the closer the pressure value moves to 0 mb, the lower the flow rate.

Of course, one or several more sophisticated algorithms such as control by proportional, integral and derivative terms (PID) could be implemented.

Furthermore, the gas delivery apparatus 1 can comprise other elements, such as a human-machine interface (HMI) with information display screen, preferably a touch screen, one or more selection keys or buttons, a starting device, such as an on/off button, an alarm system and/or other elements.

Figure 5:
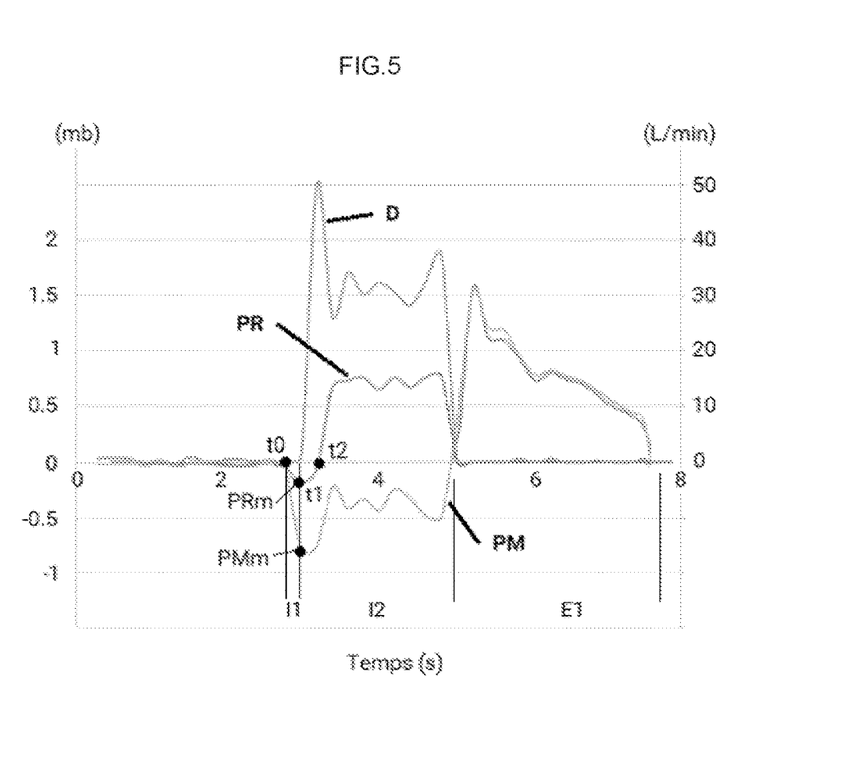
FIG. 5 illustrates the operation of the control unit of the gas delivery apparatus from FIG. 2, in particular the pressure and flow rate curves obtained over time.

FIG. 5 schematically shows the operation of the control unit 50, in particular of the algorithm implemented by the microprocessor 51 of the gas delivery apparatus 1, in response to an inhalation by the patient P.

The inhalation by the patient P is split into two successive distinct portions I1 and I2, where I1 corresponds to the very start of the inhalation. Thus, if t0 is the exact time of the start of the inhalation by the patient P, at this time the relative pressure $P_R$ in the reservoir 27 is zero, that is to say atmospheric pressure (i.e. 1 atm).

As has been mentioned above, the inhalation by the patient then creates a negative pressure in the mask 10, which is represented by the curve $P_M$. In response to this negative pressure, the control unit 50 will control the proportional valve 22 to adjust the flow rate of therapeutic gas in order to limit the pressure drop in the mask 10.

As in any system incorporating electromechanical elements, there is an intrinsic response time, that is to say a delay, in response to the physical manifestation, which here is the negative pressure in the mask 10.

During this phase I1, the pressure in the deformable reservoir 27 decreases, which is a sign that it is deflating and that a quantity of gas is circulating through the flow rate determination means 60 and the non-return valve 61 in the direction of the mask 10, in order to meet the inspiratory demand of the patient P.

At t1, this pressure decrease in the reservoir 27 reaches a minimum value $P_{Rm}$ and, similarly, a minimum pressure $P_{Mm}$ occurs in the mask 10.

This time t1 corresponds to the moment when the proportional solenoid valve 22 starts to open in response to the demand by the control unit 50 and therefore to deliver a flow rate D, marking the transition to phase I2.

In these conditions, the gas flow rate D will meet the need of the patient P and at the same time fill the reservoir 27, the pressure $P_R$ of which will increase until it returns to zero at t2, which is a sign that the reservoir 27 has returned to its rest state, that is, completely filled.

This increase in pressure $P_R$ in the reservoir 27 is naturally accompanied, at the same time, by an increase in the restored pressure $P_M$ in the mask 10, here close to approximately −0.5 mb.

The portion of phase I2 subsequent to t2 sees the reservoir 27 return to an over-inflated situation since the pressure $P_R$ is positive, which is perfectly normal.

Indeed, as has been described above, the control unit 50 controls the proportional valve 22 in such a way that the restored pressure $P_M$ in the mask 10 is as close as possible to 0 and so compensates for the losses of head of the elements situated downstream of the pressure sensor 55, in response to a flow rate measured by the flow rate determination means 60.

Finally, phase I2 gives way to an exhalation phase E1, in which the patient exhales through the exhalation port 11. This exhalation then generates a positive restored pressure $P_M$ in the mask 10, and the control unit 50 then controls the proportional valve 22 so as to interrupt the delivery of gas, that is to say the flow rate. At the same time, the reservoir 27, itself at positive pressure $P_R$, empties progressively following the profile of the pressure $P_M$ prevailing in the mask 10.

The reservoir 27 is essential to the satisfactory operation of the apparatus 1. If it was not present, the gas would circulate in rigid elements, that is to say non-deformable elements, such as the internal gas passage 100 and the gas conduit 13. Thus, during phase I1, before the proportional valve 22 opens, the patient's respiratory demand would not be satisfied, resulting in major respiratory discomfort for the patient. In addition, throughout the inhalation phase, the reservoir 27 acts as a buffer by attenuating the effect of the variations in respiratory demand of the patient P and of the response of the control unit 50 and of the proportional valve 22 to these variations.

Figure 6:
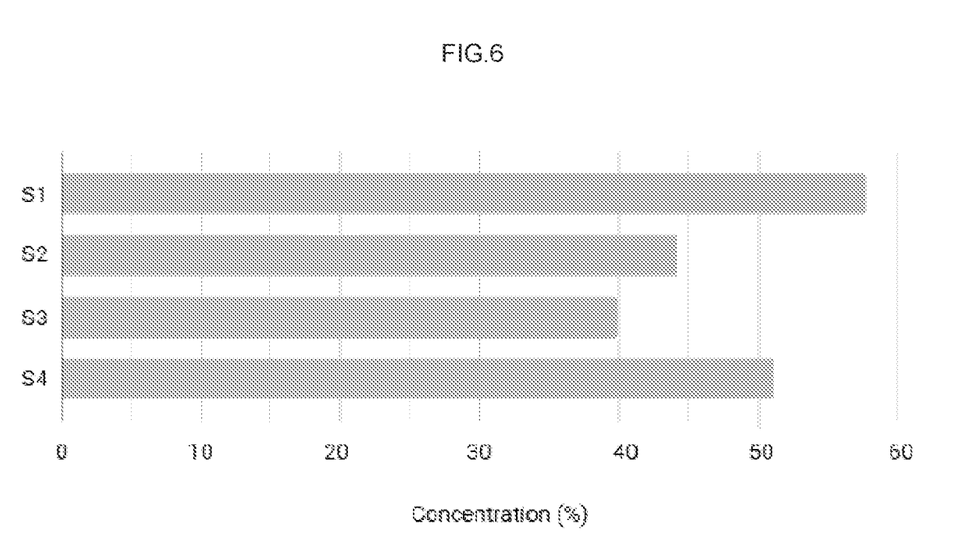
FIG. 6 is a comparison of the performance of a gas delivery apparatus according to the present invention and of several other devices.

FIG. 6 compares the performance of a gas delivery apparatus 1 according to the present invention and of several prior art devices, such as a continuous flow system and a demand valve.

In order to obtain representative data, this comparison implements a test bench comprising an "electronic patient", namely a device that mimics the respiration of a patient, for example the ASL 5000 breathing simulator available from Ingmar Medical, which makes it possible to repeatably simulate the respiration of a patient.

The different devices tested are connected to the "electronic patient" by means of a gas-conveying conduit with a calibrated orifice simulating a leak in the respiratory mask.

The therapeutic gas source supplies a mixture made up of 60% argon and 40% oxygen (vol %).

As a function of the resistance of each of the devices, and therefore of the negative pressure generated by the "electronic patient", it is possible to measure the therapeutic gas concentration inhaled by the patient under the effect of the dilution with the ambient air.

In FIG. 4:
S1 is the gas delivery apparatus 1 of the present invention, shown schematically in FIG. 1 and FIG. 2;
S2 is a demand valve, for example the GCE Ease II demand valve;
S3 is a continuous flow rate system, for example the system available from Intersurgical; and
S4 is a gas delivery apparatus similar to the apparatus of the invention (i.e. S1) but in which the system for limiting the negative pressure in the mask has been eliminated (i.e. sensor, pressure supply line, etc.).

The results obtained clearly show the limitations of the current systems.

Thus, under the effect of the simulated leak, the argon concentration inhaled by the patient P is close to 40% (vol %) for the continuous flow rate system S3 and 45% for the demand valve S2, namely a loss of 20% and 15% of argon volume respectively, which does not make it possible to ensure the efficacy of the device during delivery of gas to a patient, since the argon content supplied to the patient is far below that expected, i.e. 60 vol %.

Conversely, the gas delivery apparatus 1 (S1) of the invention makes it possible to greatly limit the dilution with ambient air, maintaining, in the same test conditions, a concentration of the order of 57 vol %, namely approximately the desired content (i.e. 60%), thus fully ensuring the therapeutic efficacy.

By way of comparison, the gas delivery apparatus 1 stripped of the means for limiting the negative pressure in the mask (S4) remains superior to the existing devices (S2, S3) but only ensures a concentration slightly greater than 50 vol %, which is insufficient to ensure efficacy of the argon treatment, for which an effective content of 60 vol % is desired.

The gas delivery apparatus 1 according to the invention therefore meets in every respect the needs of patient comfort and of minimizing the impact of leaks in terms of the reduction in the concentration of the inhaled gases, thus ensuring the desired therapeutic efficacy. This level of efficacy is possible only by combining, according to the invention, a deformable reservoir 27 with a control of the flow rate of delivered gas to the restored pressure in the mask 10, as described above.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. An apparatus (1) for delivering therapeutic gas, comprising:
   an internal gas passage (100) in fluidic communication with a deformable reservoir (27) configured for and adapted to feed the deformable reservoir (27) with a therapeutic gas and to recover the therapeutic gas coming from said deformable reservoir (27),
- a valve (22) arranged on the internal gas passage (100), upstream of the deformable reservoir (27), configured for and adapted to control a flow rate of the therapeutic gas feeding into the deformable reservoir (27),
- a control unit (50) with a microprocessor (51) configured for and adapted to control the valve (22) to set or adjust the flow rate of the therapeutic gas passing through said valve (22),
- a flow rate determination device (60) configured for and adapted to measure a pressure and/or a flow rate of the therapeutic gas in the internal gas passage (100) and to transmit a resulting measurement(s) to the control unit (50),
- a pressure sensor (55) configured for and adapted to perform one or more gas pressure measurements ($P_{55}$) on the therapeutic gas feeding the deformable reservoir (27) and to supply said gas pressure measurement(s) ($P_{55}$) to the control unit (50),
- a breathing mask (10) in fluidic communication with the internal gas passage (100) and configured for and adapted to be fed with therapeutic gas coming from the deformable reservoir (27), wherein:
the pressure sensor (55) is arranged on the internal gas passage (100) upstream of the deformable reservoir (27) and
the control unit (50) is configured for and adapted to:
a) determine the flow rate of the therapeutic gas ($Q_{60}$) circulating in the internal gas passage (100) on the basis of the resulting measurement(s) supplied by the flow rate determination device (60),
b) determine a therapeutic gas pressure on the basis of the one or more pressure measurements ($P_{55}$) on the therapeutic gas coming from the pressure sensor (55),
c) determine a loss of head ($\Delta P$) downstream of the pressure sensor (55) on the basis of the therapeutic gas flow rate ($Q_{60}$),
d) determine a pressure ($P_M$) at the breathing mask (10) on the basis of the therapeutic gas pressure and of the loss of head ($\Delta P$),
e) and control the valve (22) to adjust the therapeutic gas flow rate according to said pressure ($P_M$) determined at the breathing mask (10), to thereby adjust the pressure ($P_M$) at the breathing mask (10) to a value equal to atmospheric pressure.

2. The apparatus according to claim 1, characterized in that the control unit (50) is configured for and adapted to determine the loss of head ($\Delta P$) using a stored calculation formula: $\Delta P = R * Q_{60}^2$ wherein:
R is a constant corresponding to an equivalent resistance of all elements situated between the pressure sensor (55) and the breathing mask (10), and
$Q_{60}$ is the flow rate of the therapeutic gas ($Q_{60}$) circulating in the internal gas passage (100).

3. The apparatus according to claim 2, further comprising a computer memory for storing the formula for calculating the loss of head ($\Delta P$).

4. The apparatus according to claim 1, characterized in that the breathing mask (10) is in fluidic communication with the internal gas passage (100) via a flexible gas conduit (13).

5. The apparatus according to claim 4, characterized in that the flexible gas conduit (13) comprises a heat and humidity exchange filter.

6. The apparatus according to claim 1, characterized in that the flow rate determination device (60) is arranged downstream of the deformable reservoir (27).

7. The apparatus according to claim 1, characterized in that the flow rate determination device (60) comprises a differential pressure sensor.

8. The apparatus according to claim 1, characterized in that the valve (22) comprises a proportional valve.

9. The apparatus according to claim 1, characterized in that it further comprises at least one non-return device (61) arranged in the internal gas passage (100), downstream of the deformable reservoir (27).

10. The apparatus according to claim 1, characterized in that the control unit (50) comprises at least one electronic board carrying at least one microprocessor.

11. The apparatus according to claim 1, characterized in that the pressure sensor (55) is arranged on the internal gas passage (100) between the valve (22) and the deformable reservoir (27).

12. The apparatus according to claim 1, characterized in that the control unit (50), at least part of the internal gas passage (100), the deformable reservoir (27), the flow rate determination device (60) and the valve (22) are arranged inside a rigid outer casing (2).

13. The apparatus according to claim 1, characterized in that the breathing mask is a face mask.

14. The apparatus according to claim 1, characterized in that the pressure sensor (55) is:
i) a relative pressure sensor comprising a detection orifice (55a) arranged in the internal gas passage (100), and referenced to atmospheric pressure, and
ii) configured for and adapted to supply one or more gas pressure measurements, each corresponding to a difference between the absolute pressure determined at the detection orifice (55a) and the atmospheric pressure.

15. The apparatus according to claim 1, characterized in that a source (3) of the therapeutic gas is fluidically connected to the internal gas passage (100) and configured for and adapted to feed said gas passage (100) with the therapeutic gas, the source (3) of the therapeutic gas comprising one or more gas containers (30) comprising:
- a gas container (30) containing an $O_2/N_2O$ gas mixture or an $O_2$/argon gas mixture, or
- a first gas container (30) containing argon or $N_2O$, a second gas container (30) containing oxygen ($O_2$), and a gas mixer configured for and adapted to be fed with a gas from said first and second gas containers (30), so as to perform mixing of the gases coming from the first and second gas containers (30) and to obtain an $O_2/N_2O$ or $O_2$/argon gas mixture.

* * * * *